United States Patent
Donaldson

(10) Patent No.: US 9,265,449 B2
(45) Date of Patent: Feb. 23, 2016

(54) WEARABLE DEVICE STRUCTURE WITH ENHANCED MOTION DETECTION BY MOTION SENSOR

(71) Applicant: Thomas Alan Donaldson, London (GB)

(72) Inventor: Thomas Alan Donaldson, London (GB)

(73) Assignee: AliphCom, San Francisco, CA (US)

( * ) Notice: Subject to any disclaimer, the term of this patent is extended or adjusted under 35 U.S.C. 154(b) by 0 days.

(21) Appl. No.: 13/827,683

(22) Filed: Mar. 14, 2013

(65) Prior Publication Data

US 2014/0128751 A1    May 8, 2014

Related U.S. Application Data

(60) Provisional application No. 61/724,199, filed on Nov. 8, 2012.

(51) Int. Cl.
*A61B 5/02* (2006.01)
*A61B 5/11* (2006.01)
*A61B 5/00* (2006.01)

(52) U.S. Cl.
CPC .............. *A61B 5/11* (2013.01); *A61B 5/6824* (2013.01)

(58) Field of Classification Search
CPC ................................ A61B 5/11; A61B 5/6824
USPC .................. 600/595, 481–504; 63/3–11, 900; 24/703.1
See application file for complete search history.

(56) References Cited

U.S. PATENT DOCUMENTS

|  |  |  |  |  |
|---|---|---|---|---|
| 423,605 | A | * | 3/1890 | Harrington ....................... 63/11 |
| 4,331,154 | A | * | 5/1982 | Broadwater et al. .......... 600/490 |
| 4,338,950 | A | * | 7/1982 | Barlow et al. .................. 600/500 |
| 5,450,852 | A | * | 9/1995 | Archibald et al. ............. 600/485 |
| 5,535,603 | A | * | 7/1996 | Hayakawa .......................... 63/3 |
| 7,314,450 | B2 | * | 1/2008 | Iwamiya et al. ............... 600/503 |
| 2003/0155389 | A1 | * | 8/2003 | Swartzentruber ............. 224/164 |
| 2006/0195020 | A1 | * | 8/2006 | Martin et al. .................. 600/301 |
| 2007/0043300 | A1 | * | 2/2007 | Koblanski ..................... 600/527 |
| 2010/0076328 | A1 | * | 3/2010 | Matsumura et al. ........... 600/500 |

FOREIGN PATENT DOCUMENTS

WO    2014074951 A1    5/2014

OTHER PUBLICATIONS

Sholl, Linda, Notification of Transmittal of the International Search Report and the Written Opinion of the International Searching Authority, or the Declaration, Mailed Feb. 28, 2014 for International Patent Application No. PCT/US2013/069435, International Searching Authority.

* cited by examiner

*Primary Examiner* — Patricia Mallari
*Assistant Examiner* — Tiffany Weston
(74) *Attorney, Agent, or Firm* — Kokka & Backus, PC

(57) ABSTRACT

Techniques associated with a wearable device structure with enhanced motion detection by a motion sensor are described, including a band configured to be worn, a nodule coupled to the band, the nodule including a structure configured to enhance detection of movement of an adjacent skin surface, the structure having an articulator configured to rotate in a plurality of planes, and a sensor coupled to the structure and configured to detect rotational motion.

15 Claims, 9 Drawing Sheets

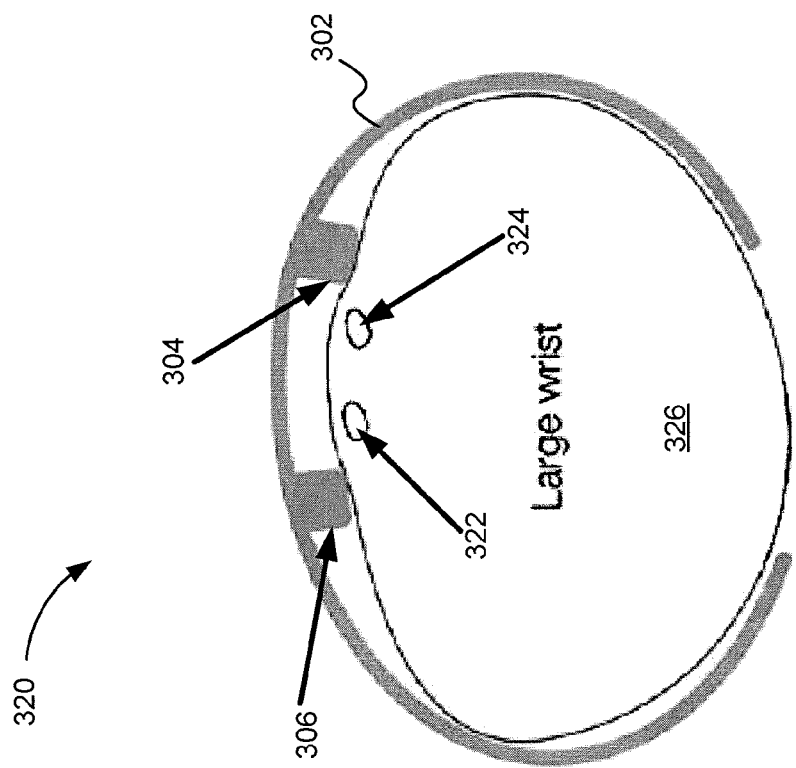
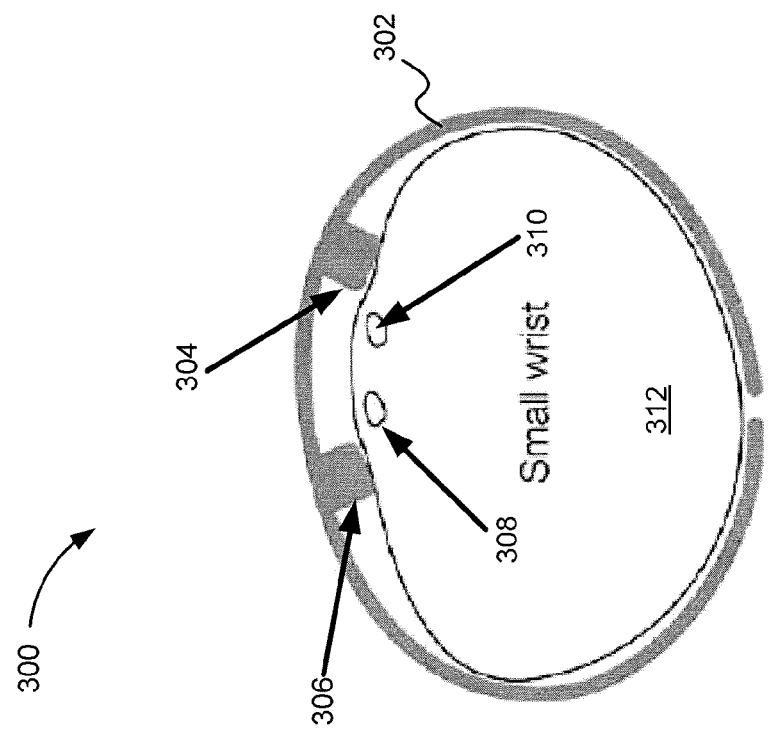
FIG. 3B
FIG. 3A ic # WEARABLE DEVICE STRUCTURE WITH ENHANCED MOTION DETECTION BY MOTION SENSOR

CROSS-REFERENCE TO RELATED APPLICATIONS

This application claims the benefit of U.S. Provisional Patent Application No. 61/724,199, filed Nov. 8, 2012, which is incorporated by reference herein in its entirety for all purposes.

FIELD

The present invention relates generally to electrical and electronic hardware, electromechanical and computing devices. More specifically, techniques related to a wearable device structure with enhanced motion detection by motion sensor are described.

BACKGROUND

Conventional techniques for a wearable device with enhanced detection by motion sensor are limited in a number of ways. Conventional implementations of motion sensors, such as accelerometers, are not well-suited for accurately detecting and measuring movement having a small linear acceleration, as may occur by displacement of a skin surface in response to a pulse in a blood vessel. In particular, accelerometers typically have a threshold sensitivity and have a difficult time measuring translations that result in accelerations close to that threshold sensitivity.

Also, conventional wearable devices are not well-suited for coupling motion sensors to particular parts of the body to detect and measure such small movements. Thus, what is needed is a solution for wearable device with enhanced detection by motion sensor without the limitations of conventional techniques.

BRIEF DESCRIPTION OF THE DRAWINGS

Various embodiments or examples ("examples") are disclosed in the following detailed description and the accompanying drawings:

FIGS. 3A-3B are diagrams depicting exemplary placement of wearable devices on a wrist;

DETAILED DESCRIPTION

Various embodiments or examples may be implemented in numerous ways, including as a system, a process, an apparatus, a device, and a method associated with a wearable device structure with enhanced detection by motion sensor. In some embodiments, motion may be detected using an accelerometer that responds to an applied force and produces an output signal representative of the acceleration (and hence in some cases a velocity or displacement) produced by the force. Embodiments may be used to couple or secure a wearable device onto a body part. Techniques described are directed to systems, apparatuses, devices, and methods for using accelerometers, or other devices capable of detecting motion, to detect the motion of an element or part of an overall system. In some examples, the described techniques may be used to accurately and reliably detect the motion of a part of the human body or an element of another complex system. In general, operations of disclosed processes may be performed in an arbitrary order, unless otherwise provided in the claims.

A detailed description of one or more examples is provided below along with accompanying figures. The detailed description is provided in connection with such examples, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

Figure 1:
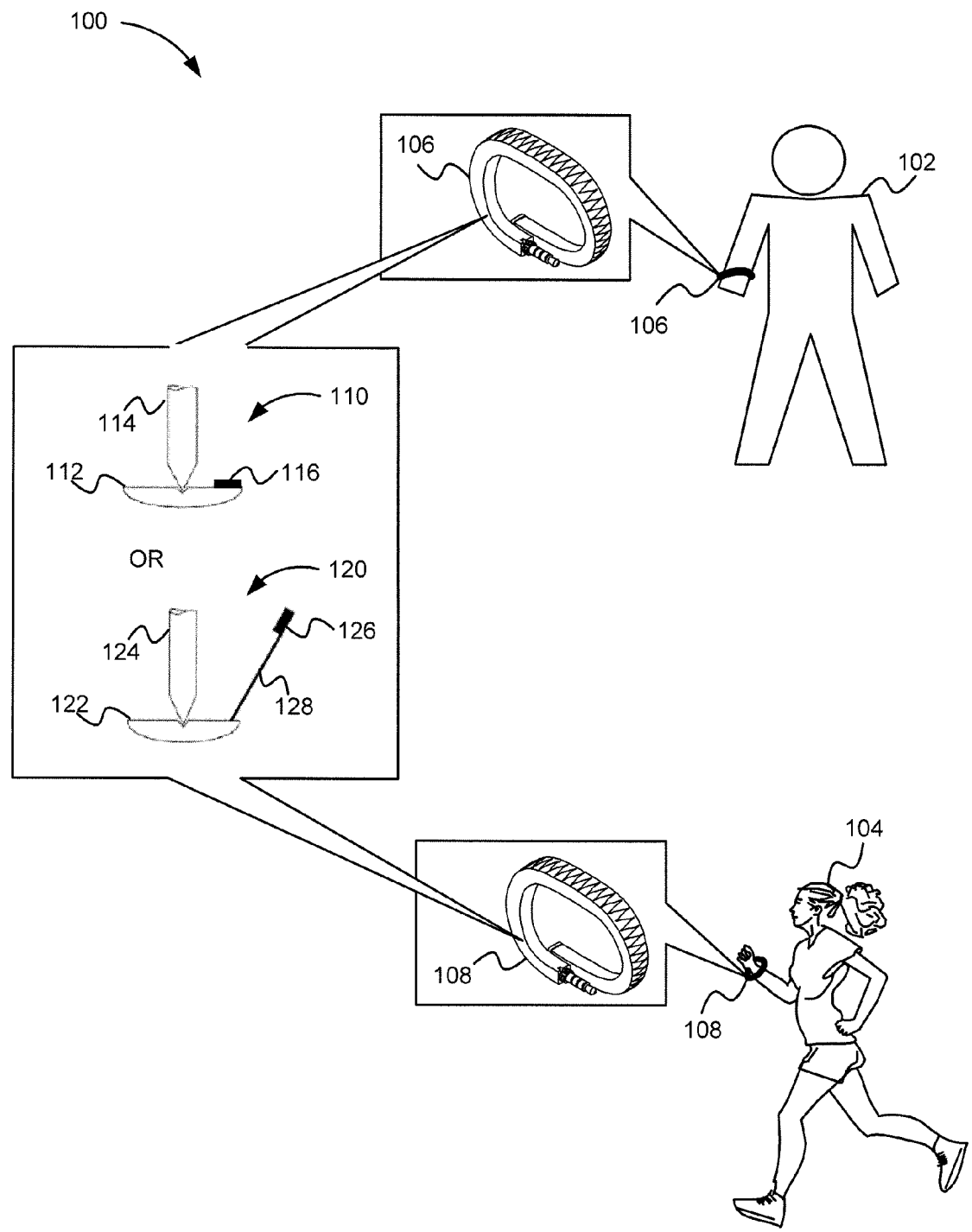
FIG. 1 is a diagram depicting exemplary wearable devices equipped with enhanced motion detection.

FIG. 1 is a diagram depicting the use of wearable devices equipped with enhanced motion detection. Here, diagram 100 includes users 102-104, wearable devices 106-108, structures 110 (including articulator 112, pin 114 and motion sensor 116) and 120 (including articulator 122, pin 124, motion sensor 126 and post 128). As shown, wearable device 106 may be worn by user 102, and wearable device 108 may be worn by user 104. In some examples, wearable devices 106-108 may be implemented as a band having one or more sensors, including motion sensors. In some examples, wearable devices 106-108 may include motion sensors configured to register and process data associated with greater movement, for example the movement of user 104, as well as smaller movement, for example the movement of user 102.

In some examples, wearable devices 106-108 may be implemented with structure 110 or structure 120 to enhance detection of motion by a motion sensor by amplifying orientation changes. In some examples, articulators 112 and 122 may be configured to transfer movement energy, for example linear movement, from a surface (i.e., skin surface) to a motion sensor. For example, articulators 112 and 122 may be configured to translate a very small linear movement on a skin surface into a rotational motion in two or more planes, which may be more easily detected by a motion sensor. Here, articulators 112 and 122 may be formed using metal, plastic, or other suitable materials (i.e., holds a shape and compatible with skin). In some examples, articulators 112 and 122 may be configured to amplify motion (i.e., using orientation changes) or to convert linear motion into rotational motion. In some examples, pins 114 and 124 may apply a force to articulators 112 and 122, respectively. As shown, pins 114 and 124 may have a pointed end that fits into a correspondingly-shaped indentation in articulators 112 and 122, respectively, for example on a pivot point (i.e., at the center of a side or on an axis of rotation), so that the force does not apply moment, or any rotational force, to articulators 112 and 122. A curved or rounded side of articulators 112 and 122 may be placed against or adjacent to a surface (i.e., skin surface) to register movement along the adjacent surface resulting in a rocking or rotation of articulators 112 and 122. In other examples, articulators 112 and 122 may be configured to rotate in two or more planes. In some examples, articulators 112 and 122 may be configured to translate small amount of linear movement (i.e., near a threshold sensitivity of an accelerometer) into a rotational movement more easily detected by a motion sensor (e.g., motion sensors 116 and 126).

In some examples, motion sensors 116 and 126 may include an accelerometer, vibration sensor (e.g., acoustic, piezoelectric, or the like), or other type of motion sensor. In some examples, motion sensors 116 may be coupled to articulators 110 by being mounted, or otherwise placed securely, onto articulator 110. In some examples, motion sensor 116 may be coupled to articulator 110 at or near an edge farther or farthest out from pin 114 so that motion sensor 116 may be subjected to, and thereby register, a greater amount of rotation, or other movement. In some examples, motion sensor 116 may be configured to register, or sense, rotational energy from articulator 110. For example, movement on a surface against which articulator 110 is being held may cause articulator 110 to rotate in one or more planes. In this example, motion sensor 116 may register and measure various characteristics (e.g., acceleration, direction, or the like) of the rotation of articulator 110. In some examples, articulator 110 may be configured to translate a small amount of linear movement (i.e., near a threshold sensitivity of an accelerometer) into a rotational movement more easily detected by motion sensor 116. For example, articulator 112 may be placed (and held) against a surface of skin adjacent to tissue, which in turn is adjacent to a blood vessel (see, e.g., FIGS. 2-4). A pulse of blood through such a blood vessel may have a small amount of linear movement that may be transferred through tissue to a skin surface against which articulator 112 may be placed such that articulator 112 may rotate in response to the movement of the blood vessel, and motion sensor 116 may capture the rotation of articulator 112.

In some examples, post 128 may be mounted, or otherwise placed securely, onto articulator 122. In some examples, post 128 may be configured to couple motion sensor 126 to articulator 122. In some examples, post 128 may be configured to extend outward from an edge of articulator 122, and away from a pivot point of articulator 122, such that motion sensor 126 may be subjected to, and thereby register, a greater amount of rotation when articulator 122 rotates in response to movement on a surface against which articulator 122 is being held. In some examples, motion sensor 126 may be configured to register, or sense, rotational energy from articulator 122. For example, movement on a surface against which articulator 122 is being held may cause articulator 122 to rotate in one or more planes. In this example, motion sensor 126 may register and measure various characteristics (e.g., acceleration, direction, or the like) of the rotation of articulator 122. In some examples, articulator 122 may be configured to translate small amount of linear movement (i.e., near a threshold sensitivity of an accelerometer) into a rotational movement more easily detected by motion sensor 126. For example, articulator 122 may be placed (and held) against a surface of skin adjacent to tissue, which in turn is adjacent to a blood vessel (see, e.g., FIGS. 2-4). A pulse of blood through such a blood vessel may have a small amount of linear movement that may be transferred through tissue to a skin surface against which articulator 122 may be placed such that articulator 122 may rotate in response to the movement of the blood vessel, and motion sensor 126 may capture the rotation of articulator 122. Additional examples of structures having an articulator coupled to a motion sensor are described in co-pending U.S. patent application Ser. No. 13/827,754, filed Mar. 14, 2013, entitled "Amplifying Orientation Changes for Enhanced Motion Detection by a Motion Sensor," which is incorporated by reference herein in its entirety for all purposes. In other examples, the quantity, type, function, structure, and configuration of the elements shown may be varied and are not limited to the examples provided.

Figure 2:
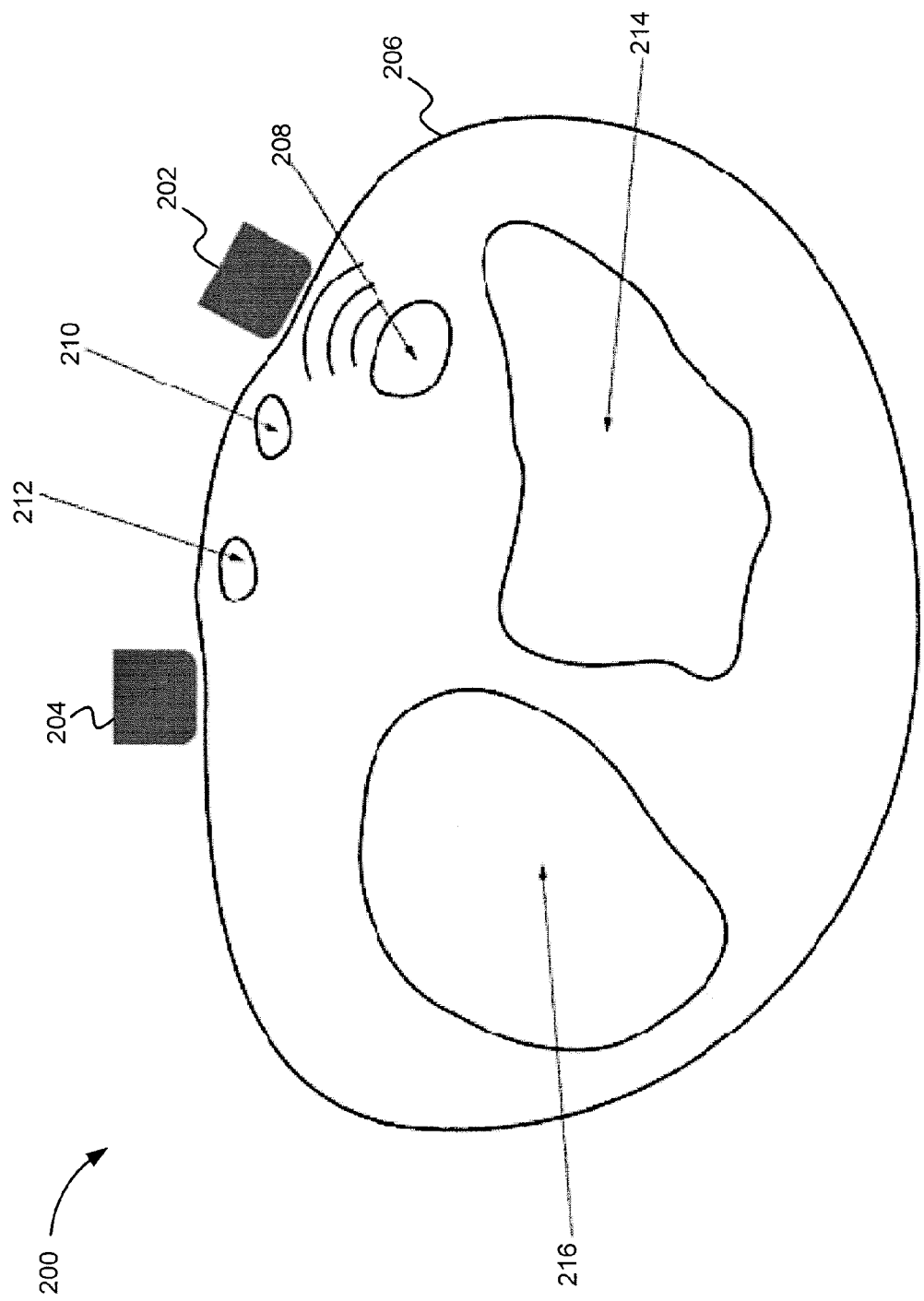
FIG. 2 is a diagram depicting exemplary placement of nodules on a wrist.

FIG. 2 is a diagram depicting exemplary placement of nodules on a wrist. Here, diagram 200 includes nodules (or nodes) 202-204, skin surface 206, blood vessel 208, tendons 210-212, bones 214-216. Like-numbered and named elements may describe the same or substantially similar elements as those shown in other descriptions. In some examples, nodules 202-204 may be coupled to, or formed integrally onto, a wearable device (not shown) such as a band wearable on a wrist (see, e.g., FIGS. 3A-3B and 6-9). In some examples, one or both of nodules 202-204 may be configured to house or hold a structure for enhancing motion detection using a motion sensor (i.e., by amplifying orientation changes), as described herein. In some examples, nodules 202-204 may be coupled to a wearable device in a position such that nodule 202 rests on skin surface 206 on one side of tendon 210 and nodule 204 rests on skin surface 206 on another side of tendon 212. For example, nodules 202-204 may be placed so as to straddle tendons 201-212 (e.g., main tendons in a wrist, including Palmaris longus and flexor carpi radialis, or the like). In some examples, a wearable device to which nodules 202-204 are coupled may be configured to exert one or more forces on nodules 202-204 to push nodules 202-204 against skin surface 206 and create dips in skin surface 206 on either side of tendons 210-212. In some examples, positioning nodules 202-204 in this way may orient a wearable device. In some examples, nodule 202 may be configured to exert a force onto blood vessel 208 to hold blood vessel 208 between nodule 202 and bone 214. For example, nodule 202 may be configured to exert a force onto skin surface 206, the force being transferred through tissue to occlude (i.e., hold, trap, keep or place) blood vessel 208 against bone 214. In some examples, positioning nodule 202 next to tendon 210 and partially or wholly over blood vessel 208 may enable a motion sensor (e.g., coupled to a structure for amplifying rotational motion) coupled to nodule 202 to register and measure a pulse traveling through blood vessel 208. In some examples, nodule 204 may be implemented with another motion sensor configured to detect motion on skin surface 206 unrelated to said pulse traveling through blood vessel 208. In some examples, a wearable device (not shown), to which nodules 202-204 may be coupled, may be configured to process data from a motion sensor in nodule 202 and another motion sensor in nodule 204 to derive characteristics or attributes associated with movement from a pulse traveling through blood vessel 208. In some examples, nodules 202-204 may be configured as, or with, electrodes using which bioimpedance may be measured and heart rate may be detected. In other examples, nodules 202-204 may be configured as, or with, piezoelectric sensors operable to acquire acoustic signals including data associated with heart rate. In other examples, the quantity, type, function, structure, and configuration of the elements shown may be varied and are not limited to the examples provided.

FIGS. 3A-3B are diagrams depicting exemplary placement of wearable devices on a wrist. Here, diagrams 300 and 320 include wearable device 302, nodules 304-306, tendons 308-310 and 322-324, small wrist 312 and large wrist 326. Like-numbered and named elements may describe the same or substantially similar elements as those shown in other descriptions. In some examples, wearable device 302 may be implemented as a band configured to be worn on a wrist. In some examples, wearable device 302 may be configured with data capabilities (e.g., data processing, communications, and the like), including circuitry (i.e., logic) for processing sensor data generated from sensors implemented in nodules 304-306, or elsewhere on wearable device 302. For example, wearable device 302 may be implemented with circuitry configured to translate data associated with rotational motion of an articulator to determine a movement (i.e., linear movement) of an adjacent surface. In another example, wearable device 302 may be configured to derive data associated with movement on an adjacent skin surface (e.g., on users 402-404's wrists, arms, or other body parts), including data associated with a direction of movement on an adjacent skin surface, a magnitude of a force exerted by a pulse in a blood vessel underneath an adjacent skin surface, a time period between two pulses, a heart rate, a blood pressure, or the like.

In some examples, nodules 304-306 may be molded integrally with wearable device 302. In other examples, nodules 304-306 may be coupled to wearable device 302 removably. In some examples, nodules 304-306 may be coupled to, or molded onto, wearable device 302 on an underside (i.e., an internal circumference, or a side facing in when wearable device 302 is worn) such that nodules 304-306 make contact, or are placed adjacent to, a body part (e.g., small wrist 312, large wrist 326, or the like) when worn. In some examples, nodules 304-306 may be coupled to, or molded onto, one or more locations on wearable device 302 in order to position nodules 304-306 on either side of tendons 308-310 or tendons 322-324, as shown (see also FIG. 2). In some examples, wearable device 302 may be formed with an original shape using a material having material memory, such that a force may be applied to deform wearable device 302 from the original shape, and when the force is removed, wearable device 302 may reassume, or return to, the original shape.

In some examples, wearable device 302 may be adjustable (e.g., by being formed of material having material memory, by implementing a magnet at each end (see FIGS. 6-8), or the like) to be worn on small wrist 312 (i.e., having a smaller circumference and smaller distance between tendons 308-310), large wrist 326 (i.e., having a larger circumference and larger distance between tendons 322-324), or other sized wrists. In some examples, wearable device 302 may form a circular shape such that when nodules 304-306 are coupled to an internal circumference of wearable device 302, nodules 304-306 point in (i.e., toward each other) when wearable device 302 is adjusted to a smaller circumference, and point farther away from each other when wearable device 302 is adjusted to a larger circumference. For example, in FIG. 3A, when wearable device 302 is worn on small wrist 312, nodules 304-306 may point in toward each other, and thereby adjust to a smaller distance between tendons 308 and 310. In another example, in FIG. 3B, when wearable device 302 is worn on large wrist 326, nodules 304-306 may point farther away from each other (i.e., distance between the internal edges of nodules 304-306 is greater), and thus adjust to a larger distance between tendons 322-324. In other examples, the quantity, type, function, structure, and configuration of the elements shown may be varied and are not limited to the examples provided.

Figure 4:
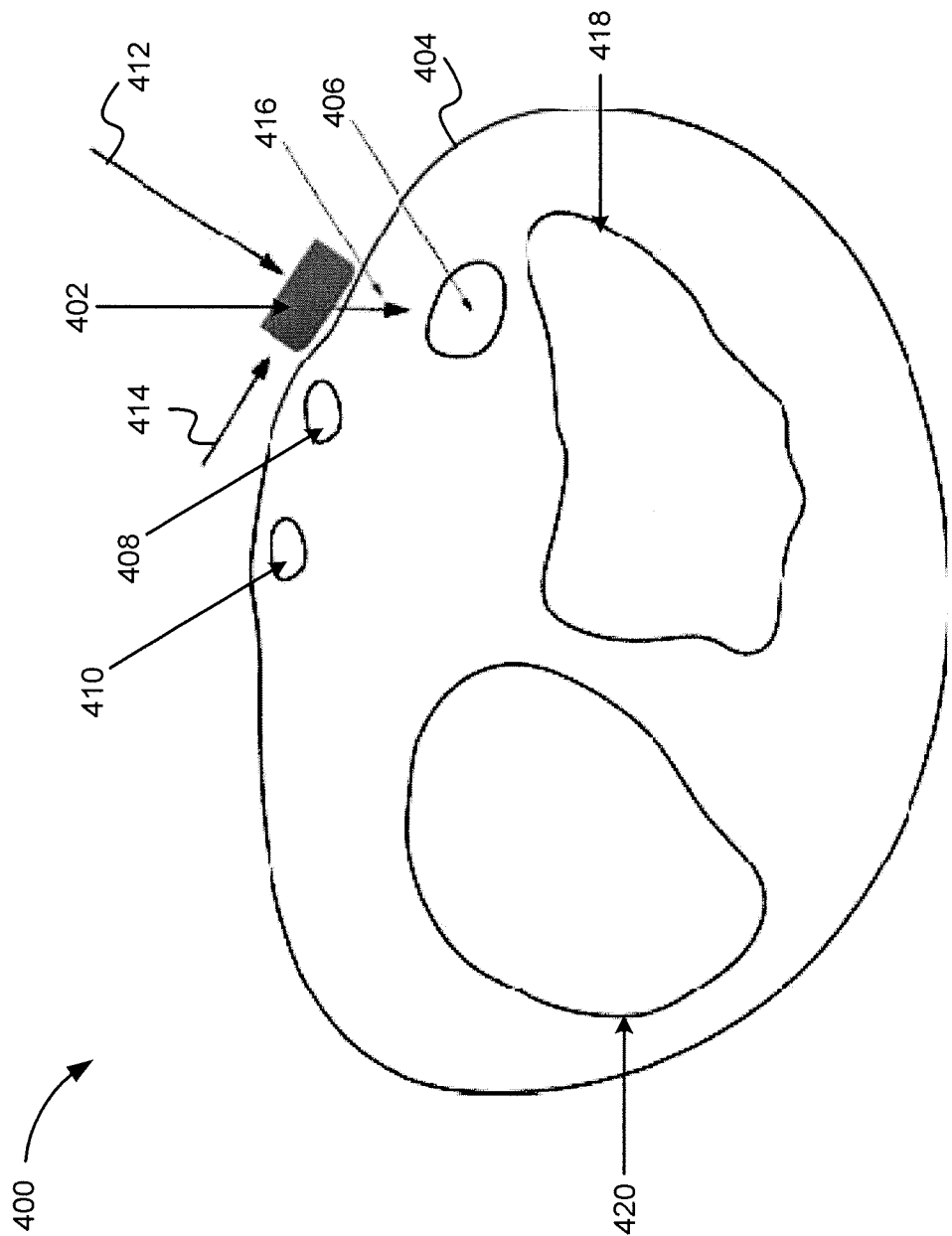
FIG. 4 is a diagram depicting exemplary placement of a nodule on a wrist.

FIG. 4 is a diagram depicting exemplary placement of a nodule on a wrist. Here, diagram 400 includes nodule 402, skin surface 404, blood vessel 406, tendons 408-410, forces 412-416 and bones 418-420. Like-numbered and named elements may describe the same or substantially similar elements as those shown in other descriptions. In some examples, nodule 402 may include, or be implemented to house, a structure for enhancing motion detection (i.e., through amplification of orientation changes in a motion sensor, as described herein). For example, nodule 402 may have an articulator (e.g., articulators 112 and 122 in FIG. 1) against skin surface 404. In some examples, nodule 402, or a wearable device (e.g., wearable devices 106-108 in FIG. 1, wearable device 302 in FIGS. 3A-3B, or the like) to which nodule 402 may be coupled, may be configured to apply forces 412-414, force 412 being a radial force directed toward the center of a limb (i.e., as may be enclosed by skin surface 404), and force 414 being a circumferential force, or other tangential force (i.e., parallel to skin surface 404 at a location adjacent to articulator 402). In some examples, forces 412-414 act to couple nodule 402 with skin surface 404 by generating a resulting force 416. In some examples, a motion sensor (e.g., motion sensors 116 and 126 in FIG. 1) may be implemented in, or coupled to, nodule 402 to sense rotational movement, for example of an articulator (e.g., articulators 112 and 122 in FIG. 1) included in, mounted on, or coupled to nodule 402. In some examples, nodule 402 may be used to implement a structure configured to amplify orientation changes caused by movement of skin surface 404 resulting from a pulse traveling through blood vessel 408. In other examples, the quantity, type, function, structure, and configuration of the elements shown may be varied and are not limited to the examples provided.

Figure 5:
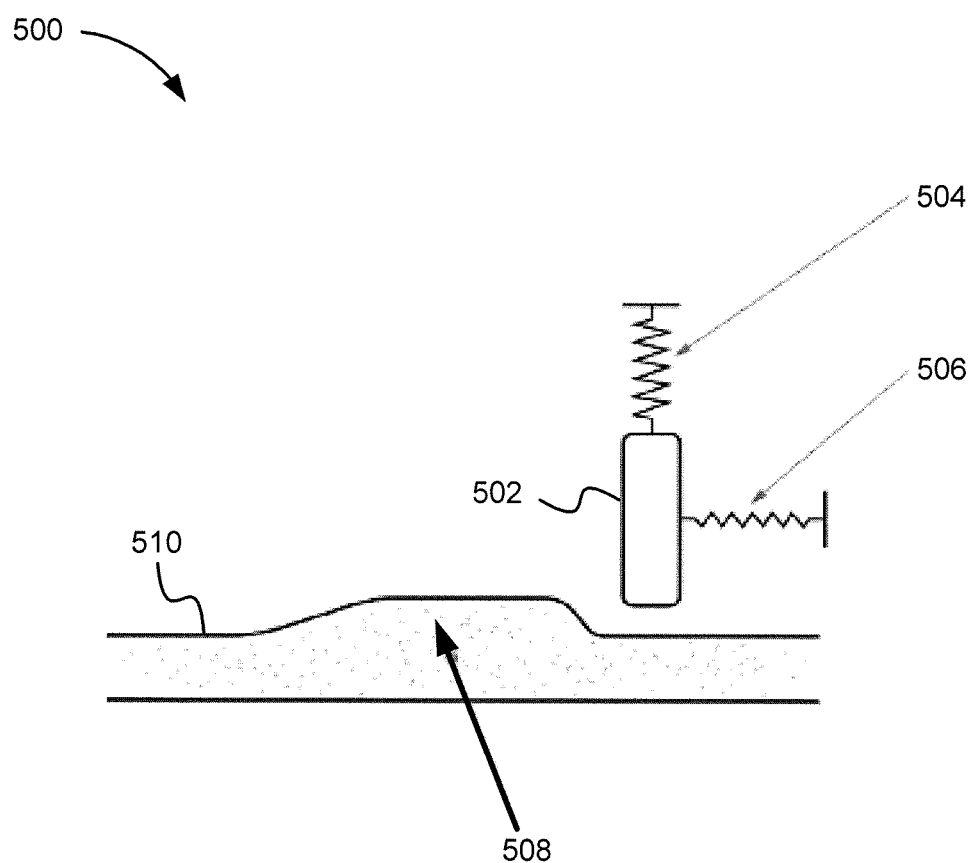
FIG. 5 is a diagram depicting an exemplary spring structure coupled to a nodule.

FIG. 5 is a diagram depicting an exemplary spring structure coupled to a nodule. Here, diagram 500 includes nodule 502, springs 504-506, pulse 508 and blood vessel 510. Like-numbered and named elements may describe the same or substantially similar elements as those shown in other descriptions. In some examples, nodule 502 may be coupled to a wearable device (e.g., wearable devices 106-108 in FIG. 1, wearable device 302 in FIGS. 3A-3B, or the like) using springs 504-506. In some examples, spring 504 may be a relatively strong spring configured to apply a larger force than spring 506. In some examples, spring 504 may be configured to apply a force perpendicular to blood vessel 510. In some examples, spring 506 may be configured to apply a tangential force, parallel to blood vessel 510. Forces applied by springs 504-506 may serve to hold nodule 502 against a surface (i.e., skin surface) (e.g., skin surface 206 in FIG. 2, skin surface 404 in FIG. 4, or the like), and may cause nodule 502 to create a dip in a skin surface, as described above. In some examples, spring 504 may apply a force configured to hold blood vessel 510 in a place or against a bone (e.g., bone 214 in FIG. 2, bone 418 in FIG. 4, or the like). In some examples, spring 506 may apply a weaker force than spring 504, in a different or opposite direction from an acceleration associated with pulse 508. In some examples, spring 506 may compress in response to pulse 508 traveling through blood vessel 510. In some examples, nodule 502 may be implemented with sensors (e.g., motion sensors 116 and 126 in FIG. 1) configured to detect and measure acceleration resulting from, or otherwise associated with, pulse 508 (i.e., using a structure for amplifying rotational motion, as described herein). In other examples, the quantity, type, function, structure, and configuration of the elements shown may be varied and are not limited to the examples provided.

Figure 6:
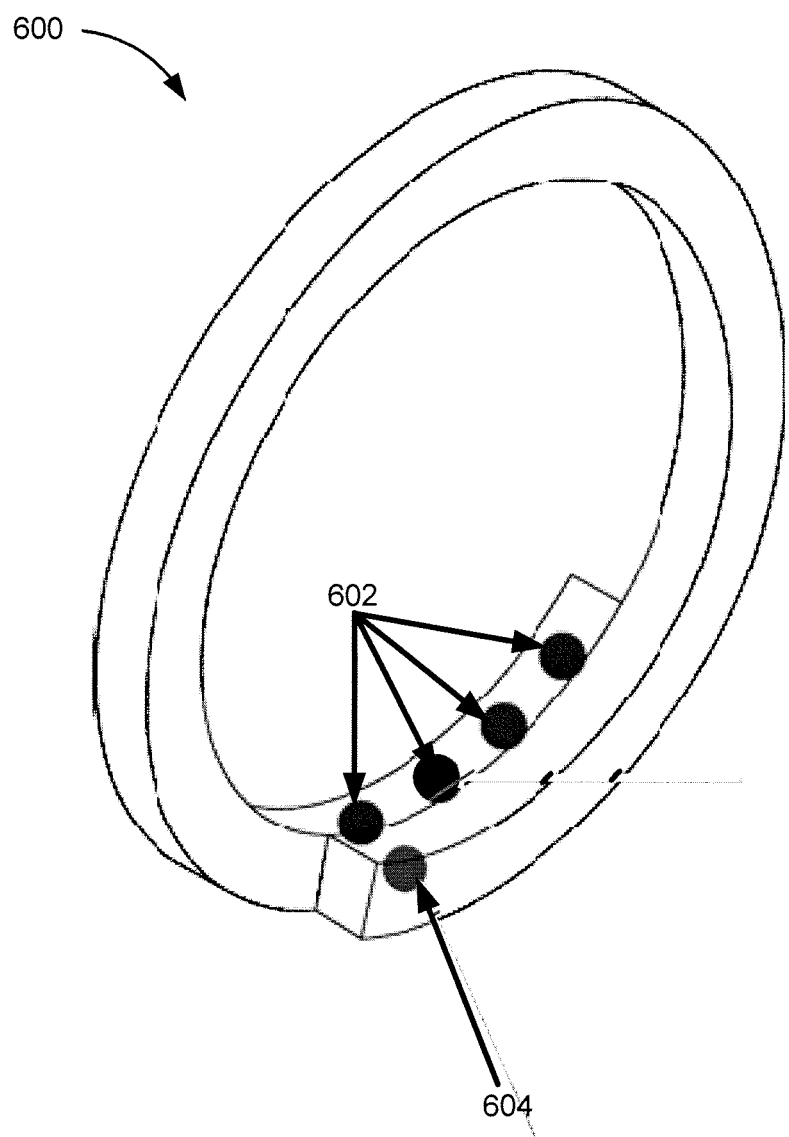
FIG. 6 illustrates an exemplary adjustable wearable device.

FIG. 6 illustrates an exemplary adjustable wearable device. Here, wearable device 600 includes magnet array 602 and magnet 604. Like-numbered and named elements may describe the same or substantially similar elements as those shown in other descriptions. In some examples, wearable device 600 may comprise a flexible band configured to be placed around a limb, such as a wrist. In some examples, magnet array 602 may include two or more magnets, a first magnet disposed at or near a first end of wearable device 600, and subsequent magnets in magnet array 602 disposed serially up the length of wearable device 600. In some examples, magnet 604 may be disposed at or near a second, or opposite, end of wearable device 600. In some examples, magnet 604 may be configured to attract each of the magnets in magnet array 602, thereby adjustably closing the first end of wearable device 600 with the second end. For example, a first end of wearable device 600 may be brought into proximity with a second end of wearable device 600, which may in turn bring magnet 604 (i.e., disposed in the second end) in proximity with a first magnet in magnet array 602 disposed closest to the first end, the magnetic attraction between magnet 604 and the first magnet in magnet array 602 bring the first end and the second end together to close wearable device (i.e., by securing the first end against the second end) into a larger loop (i.e., to encircle a larger wrist). As shown, magnet 604 may be brought into proximity with a fourth or last magnet in magnet array 602 disposed farther from the first end, and closing or securing wearable device 600 into a smaller loop (i.e., to encircle a smaller wrist). In other examples, magnet 604 may be used to attract other magnets in magnet array 602 to create different sized loops for wearing on different sized wrists. In still other examples, the quantity, type, function, structure, and configuration of the elements shown may be varied and are not limited to the examples provided.

Figure 7:
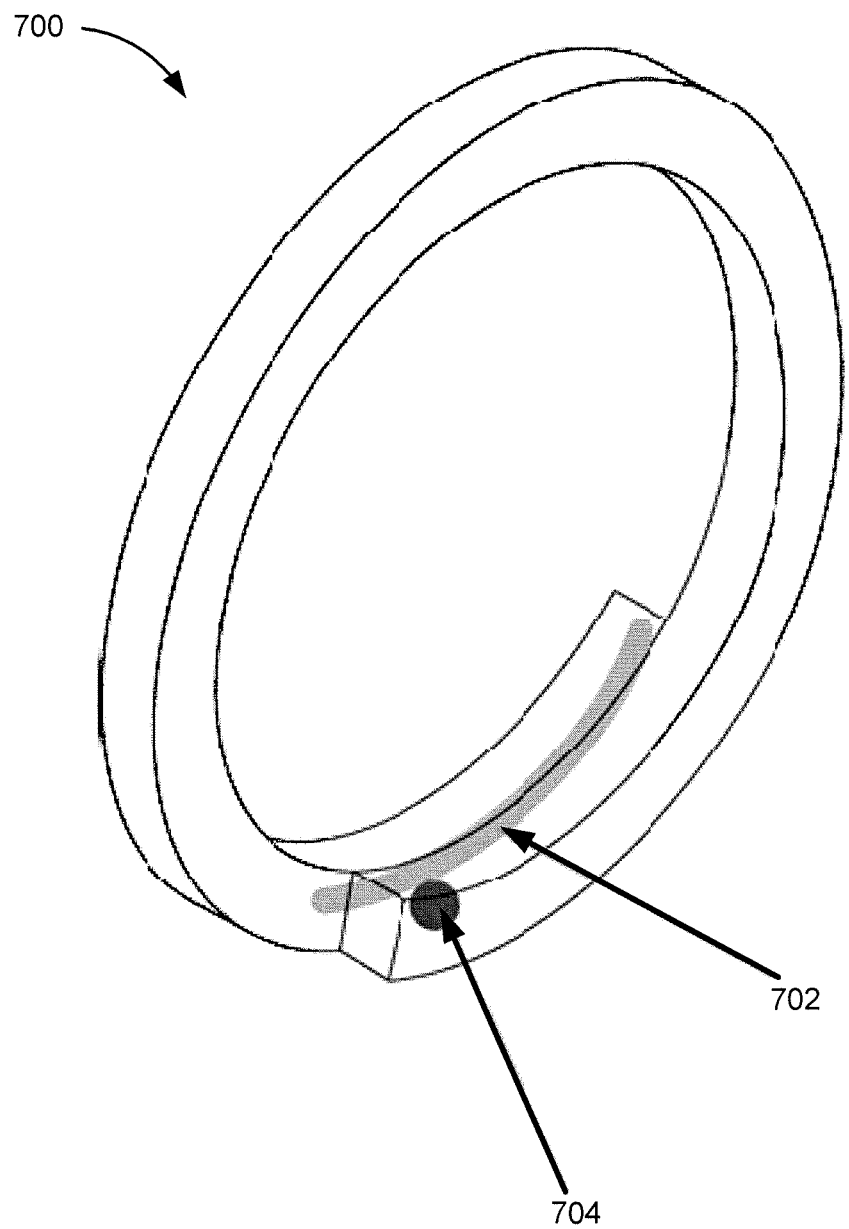
FIG. 7 illustrates an alternative exemplary adjustable wearable device.

FIG. 7 illustrates an alternative exemplary adjustable wearable device. Here, wearable device 700 includes strip 702 and magnet 704. Like-numbered and named elements may describe the same or substantially similar elements as those shown in other descriptions. In some examples, strip 702 may be formed using a metal (e.g., stainless steel or the like) or other ferromagnetic material, to which magnet 704 may attract. In some examples, wearable device 700 may have a first end and a second, or opposite, end. In some examples, strip 702 may be disposed along a length of wearable device 700 starting in a first end, and magnet 704 may be disposed at a second, or opposite, end. In some examples, strip 702 and magnet 704 may be configured to adjustably close (i.e., secure) wearable device 700 around a wrist using an attraction between strip 702 and magnet 704. In some examples, magnet 704 may be attracted to any portion of strip 702, and thus moved along a length of wearable device 700 in which strip 702 may be disposed in order to expand or contract the size of wearable device 700. In still other examples, the quantity, type, function, structure, and configuration of the elements shown may be varied and are not limited to the examples provided.

Figure 8A:
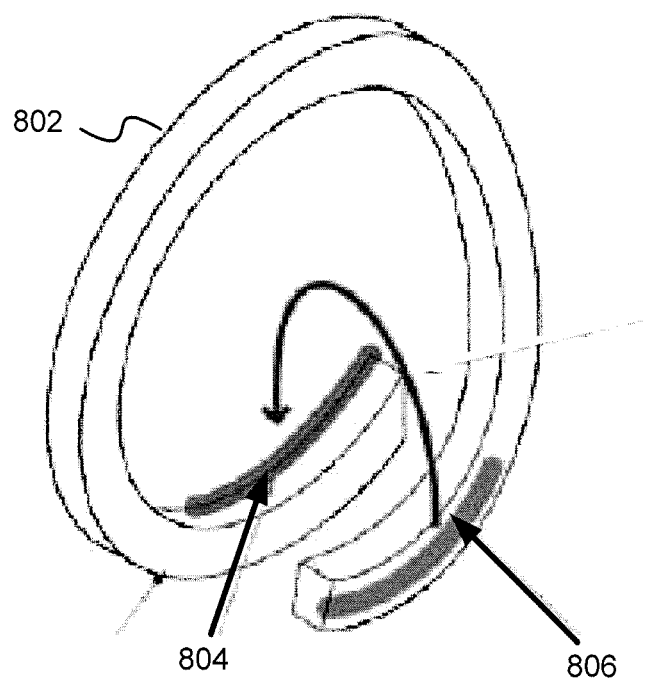
FIG. 8A-8B illustrates an exemplary wearable device formed with tension.
Figure 8B:
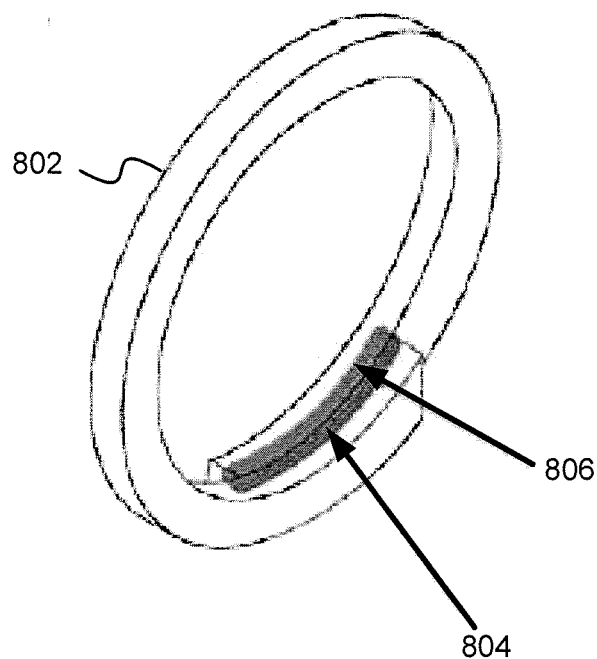

FIG. 8A-8B illustrates an exemplary wearable device formed with tension. Here, wearable device 802 includes interface materials 804-806. Like-numbered and named elements may describe the same or substantially similar elements as those shown in other descriptions. In some examples, wearable device 802 may be molded with an amount of tension in an open position, as shown in FIG. 8A, the tension causing two ends of wearable device 802 to resist being pushed or pulled together. In some examples, interface material 804 may be molded onto, or coupled with, one side of one end of wearable device 802, and interface material 806 may be molded onto, or coupled with, another side of another end of wearable device 802, the one side and the another side configured to be brought together to hold wearable device 802 in a closed position. In some examples, interface material 804 and interface material 806 may be disposed such that the one side (i.e., on which interface material 804 is disposed) and the another side (i.e., on which interface material 806 is disposed) face each other when band 802 is in a closed position. In some examples, interface materials 804-806 may be configured to have high friction to hold the one side and the another side together in a closed position. For example, interface materials 804-806 may be formed using a high friction material (e.g., rubber, polymer, or the like). In another example, interface materials 804-806 may be formed with a high friction structure (e.g., corrugated, hook and loop, or the like). In other examples, the one side and the another side may be different sides than shown. In still other examples, the quantity, type, function, structure, and configuration of the elements shown may be varied and are not limited to the examples provided.

Figure 9:
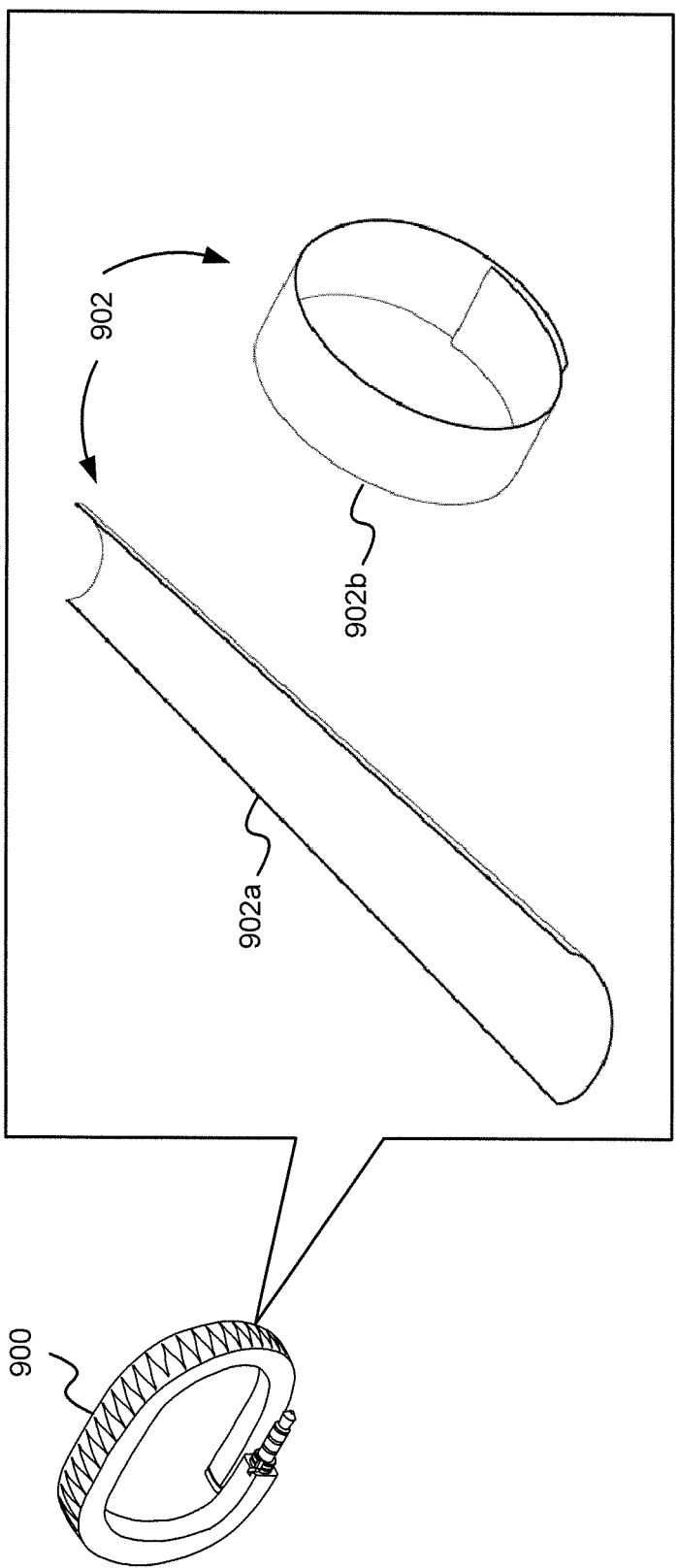
FIG. 9 illustrates an exemplary wearable device formed with a bistable structure.

FIG. 9 illustrates an exemplary wearable device formed with a bistable structure. Here, wearable device 900 may be formed using bistable band 902 (shown in positions 902a and 902b). Like-numbered and named elements may describe the same or substantially similar elements as those shown in other descriptions. In some examples, bistable band 902 may be formed using a bistable material configured to rest in two different states, for example, in position 902a (i.e., an open position) and in position 902b (i.e., a closed position). In some examples, bistable band 902 may be formed using steel (i.e., stainless steel) pre-formed into position 902a, which is able to curl into position 902b to close around a wrist, or other body part. In some examples, bistable band 902 may be configured to curl into position 902b in response to a force exerted against a region of bistable band 902, as may result when bistable band 902 in position 902a is slapped against a wrist. In other examples, the quantity, type, function, structure, and configuration of the elements shown may be varied and are not limited to the examples provided.

Although the foregoing examples have been described in some detail for purposes of clarity of understanding, the above-described inventive techniques are not limited to the details provided. There are many alternative ways of implementing the above-described invention techniques. The disclosed examples are illustrative and not restrictive.

What is claimed is:

1. A method, comprising:
coupling a first nodule to a skin surface at a location, the first nodule formed in a wearable device comprising a structure configured to enhance detection of movement of the skin surface adjacent a first blood vessel, the structure comprising an articulator configured to rotate in a plurality of planes and the first nodule comprising a sensor configured to detect a bioimpedance measurement derived from an electrical current measured at the skin surface;
detecting rotation motion caused by the articulator using an accelerometer coupled to the articulator;
deriving data associated with the movement of the skin surface from the rotation motion caused by the articulator; and
coupling a second nodule formed in the wearable device to the skin surface at another location, the second nodule comprising another accelerometer configured to detect other movement on the skin surface adjacent a second blood vessel, the other movement unrelated to the movement being enhanced by the structure,
wherein the wearable device is configured to maintain the first nodule adjacent to the first blood vessel and the second nodule adjacent to the second blood vessel during movement of the wearable device.

2. The method of claim 1, wherein deriving data associated with the movement of the skin surface comprises deriving an attribute associated with a blood vessel residing beneath the skin surface.

3. The method of claim 1, wherein the first nodule is configured to rest against an adjacent skin surface next to a tendon.

4. The method of claim 1, wherein the second nodule is configured to rest against an adjacent skin surface to another side of a tendon.

5. The method of claim 1, wherein the first nodule is configured to exert a force on an adjacent skin surface, the force being transferred through tissue to occlude a blood vessel against a bone.

6. The method of claim 1, wherein the first nodule and the second nodule are configured to rest on an adjacent skin surface to opposite sides of one or more tendons on a wrist.

7. The method of claim 1, wherein the structure is configured to translate movement from a pulse traveling through a blood vessel into a rotation in one or more of the plurality of planes.

8. The method of claim 1, further comprising deriving from data associated with movement of the articulator a direction of movement on an adjacent skin surface.

9. The method of claim 1, further comprising deriving from data associated with movement of the articulator a magnitude of a force exerted by a pulse in a blood vessel underneath the adjacent skin surface.

10. The method of claim 1, further comprising deriving from data associated with movement of the articulator a time period between two pulses in a blood vessel.

11. The method of claim 1, further comprising deriving from data associated with movement of the articulator a heart rate.

12. The method of claim 1, further comprising deriving from data associated with movement of the articulator a blood pressure.

13. The method of claim 1, wherein the first module is integrally molded with a band.

14. The method of claim 1, wherein deriving data associated with the movement of the skin surface comprises deriving an attribute associated with a blood vessel residing beneath the skin surface, the attribute further comprises a blood pressure.

15. The method of claim 1, wherein deriving data associated with the movement of the skin surface comprises deriving an attribute associated with a blood vessel residing beneath the skin surface, the attribute further comprises a time period between two pulses in the blood vessel.

* * * * *